United States Patent [19]

Roantree et al.

[11] 4,359,466

[45] Nov. 16, 1982

[54] GUANIDINE COMPOUNDS

[75] Inventors: Michael L. Roantree, Welwyn Garden City; Rodney C. Young, Bengeo, both of England

[73] Assignee: Smith Kline & French Laboratories Limited, Welwyn Garden City, England

[21] Appl. No.: 196,502

[22] Filed: Oct. 14, 1980

[51] Int. Cl.³ .................. C07D 277/20; A61K 31/425
[52] U.S. Cl. .................................. 424/263; 424/270; 424/274; 548/198
[58] Field of Search ............... 424/263, 269, 270, 274; 548/198

[56] References Cited

U.S. PATENT DOCUMENTS

| | | | |
|---|---|---|---|
| 4,165,377 | 8/1979 | Jones et al. | 424/270 |
| 4,165,378 | 8/1979 | Gilman et al. | 424/270 |
| 4,238,494 | 12/1980 | Roantree et al. | 424/263 |

FOREIGN PATENT DOCUMENTS 10894  10/1978  European Pat. Off. .

*Primary Examiner*—Nicholas S. Rizzo
*Attorney, Agent, or Firm*—Joan S. Keps; Richard D. Foggio; Alan D. Lourie

[57] ABSTRACT

The compounds of this invention are 2-(2-guanidino-4-thiazolyl alkylamino)-3-nitropyrroles which have histamine $H_2$-antagonist activity.

12 Claims, No Drawings

GUANIDINE COMPOUNDS

This invention relates to guanidine compounds having histamine $H_2$-antagonist activity, pharmaceutical compositions containing them and methods of blocking histamine $H_2$-receptors by administering these compounds.

Histamine, a physiologically active compound endogenous in mammals, exerts its action by interacting with certain sites called receptors. One type of receptor is known as a histamine $H_1$-receptor (Ash and Schild, Brit. J. Pharmac. 1966, 27, 427) and the actions of histamine mediated through these receptors are blocked by drugs commonly called "antihistamines" (histamine $H_1$-antagonists) a common example of which is mepyramine. A second type of histamine receptor is known as the $H_2$-receptor (Black et al. Nature 1972, 236, 385). These receptors are not blocked by mepyramine but are blocked by burimamide. Compounds which block these histamine $H_2$-receptors are called histamine $H_2$-antagonists.

Histamine $H_2$-antagonists are useful in treating disease conditions caused by the biological effects of histamine mediated through $H_2$-receptors, for example, as inhibitors of gastric acid secretion, in the treatment of inflammation mediated through histamine $H_2$-receptors and as agents which act on the cardiovascular system, for example, as inhibitors of effects of histamine on blood pressure mediated through histamine $H_2$-receptors.

Cimetidine is an example of a histamine $H_2$-antagonist. Cimetidine has been shown to be useful in the treatment of duodenal, gastric, recurrent and stomal ulceration, and reflux oesophagitis and in the management of patients who are at high risk from haemorrhage of the upper gastrointestinal tract.

In some physiological conditions the biological actions of histamine are mediated through both histamine $H_1$ and $H_2$-receptors and blockade of both types of receptors is useful. These conditions include inflammation mediated by histamine, for example skin inflammation, and those hypersensitivity responses due to the action of histamine at $H_1$- and $H_2$-receptors, for example allergies.

A class of guanidine derivatives has now been discovered which are particularly active as histamine $H_2$-antagonists.

Accordingly, the present invention provides compounds of formula (I):

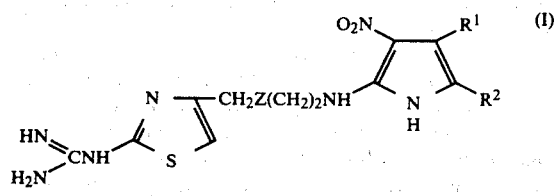

or pharmaceutically acceptable acid addition salt thereof, where Z is sulphur or methylene and $R^1$ is hydrogen; $C_{1-4}$ alkyl; optionally substituted phenyl or phenyl ($C_{1-4}$ alkyl) (the substituents being one or more $C_{1-4}$ alkyl, or $C_{1-4}$ alkoxy groups or halogen atoms or a methylenedioxy group); or optionally substituted furanyl-, thienyl-, or pyridyl- ($C_{1-4}$ alkyl) (the substituents being one or more $C_{1-4}$ alkyl or $C_{1-4}$ alkoxy groups); and $R^2$ is hydrogen, $C_{1-4}$ alkyl or benzyl.

Examples of substituted phenyl groups and the substituted phenyl moiety of phenyl ($C_{1-4}$ alkyl) groups for $R^1$ are 3-methylphenyl; 3-methoxyphenyl; 3,4-dimethoxyphenyl and 3-chlorophenyl.

Examples of optionally substituted furanyl, thienyl and pyridyl ($C_{1-4}$ alkyl) groups for $R^1$ are optionally substituted 2-furanyl-, 2-thienyl-, 2-pyridyl-, 3-pyridyl-, or 4-pyridyl-($C_{1-4}$ alkyl) groups, and particularly 3-pyridyl-, 6-methyl-3-pyridyl- and 6-methoxy-3-pyridyl-($C_{1-4}$ alkyl).

Preferably $R^1$ is hydrogen.
Preferably $R^2$ is hydrogen.
Preferably Z is sulphur.

Pharmaceutically acceptable acid addition salts of the compounds of formula (I) include those formed with hydrochloric, hydrobromic, hydroiododic, sulphuric and maleic acids.

Preferably the compound is in the form of the free base.

The compounds of the invention can be prepared by reacting a compound of formula (II):

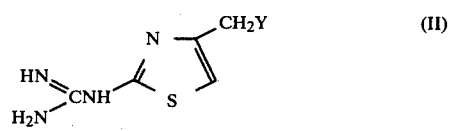

where Y is either $Z(CH_2)_2NH_2$ or, when Z in the compound of formula (I) is sulphur, a leaving group displaceable by mercaptan, with a compound of formula (III):

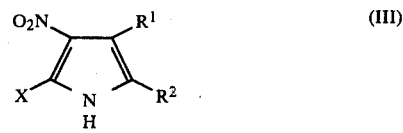

where X is a leaving group displaceable with an amine when Y is $Z(CH_2)_2NH_2$, or $HS(CH_2)_2NH$— when Y is a leaving group displaceable by mercaptan; and $R^1$ and $R^2$ are as defined with reference to formula (I), and thereafter optionally converting the compound of formula (I) so obtained into a salt.

Examples of leaving groups displacable by mercaptan are halogen, trisubstituted phosphonium (for example tri-phenylphosphonium) or substituted sulphonyloxy (for example, p-toluenesulphonyloxy, methanesulphonyloxy or trifluoromethanesulphonyloxy).

Examples of leaving groups displacable by amines are where X is QSO- or $QSO_2$- (Q being $C_{1-4}$ alkyl, aryl or aralkyl). Preferably the group X is QSO where Q is methyl or benzyl.

The process where X is a leaving group displaceable by amines is preferably carried out in the presence of a solvent, for example a $c_{1-4}$ alkanol. In general, an elevated temperature will be used, for example, the boiling point of the reaction mixture.

Acid addition salts of compounds of formula (I) can conveniently be formed from the corresponding bases by standard procedures for example by reacting the base with an acid in a $C_{1-4}$ alkanol or by the use of ion exchange resins to form the required salt. Salts of compounds of formula (I) can also be interconverted using an ion exchange resin.

The compounds of formula (I) and the intermediate compounds of formula (III) where X is QSO- or QSO$_2$- can be prepared by reacting a compound of formula (IV):

where E is

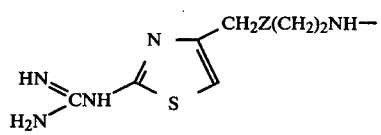

or QS- and X$^1$ is QS, or QSO when E is QS-, with a compound of formula (V):

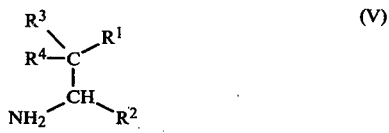

where R$^1$ and R$^2$ are as defined with reference to formula (I) and R$^3$ and R$^4$ are C$_{1-4}$ alkoxy groups or together represent an oxygen atom; optionally converting a compound of formula (I) so obtained into a salt or oxidizing a compound of formula (III) so obtained where X is QS-.

When compound (V) is used, where R$^3$ and R$^4$ together represent an oxygen atom, the reaction will in general be carried out under basic conditions, for example with sodium ethoxide in ethanol. When a compound (V) is used where R$^3$ and R$^4$ are C$_{1-4}$ alkoxy, the reaction is preferably carried out under neutral conditions, for example, in boiling ethanol, and the product cyclised under acidic conditions, for example by treatment with hydrogen chloride in a solvent (for example ether or a C$_{1-4}$ alkanol).

An intermediate (III) obtained by this process where X is QS- can be oxidised with one equivalent of hydrogen peroxide, to an intermediate (III) where X is QSO- and to an intermediate (III) where X is QSO$_2$- by reaction with two or more equivalents of hydrogen peroxide.

The intermediates of formula (III) where X is HS(CH$_2$)$_2$NH- can be prepared by reacting a compound of formula (III) where X is QSO- or QSO$_2$- with an amine of formula HS(CH$_2$)$_2$NH$_2$.

The activity of the compounds of formula (I) as histamine H$_2$- antagonists can be demonstrated by the inhibition of histamine-stimulated secretion of gastric acid from the lumen-perfused stomachs of rats anaesthetised with urethane. This procedure is referred to in Ash and Schild, Brit. J. Pharmac. Chemother., 1966. 27. 247 The compound of Example 1 hereafter caused 50% inhibition of maximal acid secretion at doses of less than 0.1 micromole kg$^{-1}$ i.v. Their activity as histamine H$_2$-antagonists can also be demonstrated by their ability to inhibit other actions of histamine which, according to the above mentioned paper of Ash and Schild, are not mediated by histamine H$_1$-receptors. For example, they inhibit the actions of histamine on the isolated guinea pig atrium. The potency of these compounds is illustrated by the effective dose producing 50% inhibition of the histamine-induced tachycardia in the isolated guinea pig atrium (less than 10$^{-6}$ Molar for compound of Example 1).

In order to use compounds of formula (I) or a pharmaceutically acceptable salt thereof for medical purposes, they are normally formulated in accordance with standard pharmaceutical practice as pharmaceutical compositions.

The invention further provides pharmaceutical compositions comprising a compound of formula (I) above or a pharmaceutically acceptable acid addition salt thereof together with a pharmaceutically acceptable carrier.

Compounds of formula (I) and their pharmaceutically acceptable acid addition salts may be administered orally, parenterally, cutaneously or rectally.

Compounds of formula (I) and their pharmaceutically acceptable salts which are active when given orally can be formulated as syrups, tablets, capsules and lozenges. A syrup formulation will generally consist of a suspension or solution of the compound or salt in a suitable liquid carrier for example, ethanol glycerine or water with a flavouring or colouring agent. Where the composition is in the form of a tablet, any suitable pharmaceutical carrier routinely used for preparing solid formulations may be used. Examples of such carriers include magnesium stearate, starch, lactose, sucrose and cellulose.

Typical parenteral compositions consist of a solution or suspension of the compound or salt in a sterile aqueous carrier or parenterally acceptable oil.

Typical compositions for administration to the skin include lotions and creams in which the compound of formula (I) or salt thereof is contained in a liquid vehicle.

A typical suppository formulation comprises a compound of formula (I) or a pharmaceutically acceptable salt thereof which is active when administered in this way, with a binding and/or lubricating agent such as gelatin or cocoa butter or other low melting vegetable waxes or fats.

Preferably the composition is in unit dose from such as a tablet or capsule.

Each dosage unit contains preferably from 15 to 250 mg of a compound of formula (I) or a pharmaceutically acceptable salt thereof calculated as the free base.

This invention also provides a method of blocking histamine H$_2$-receptors which comprises administering to an animal an effective amount to block said receptors of a compound of formula (I).

The pharmaceutical compositions of the invention will normally be administered to man for the treatment of peptic ulcers and other conditions caused or exacerbated by gastric acidity in the same general manner as that employed for known histamine H$_2$-antagonists, due allowance being made in terms of dose levels for the potency of the compound of the present invention relative to known histamine H$_2$-antagonists. The daily dosage regimen for an adult patient is an oral dose of between 15 mg and 1500 mg and preferably between 20 mg and 250 mg or an intravenous, subcutaneous or intramuscular dose of between 1.5 mg and 150 mg, and preferably between 5 mg and 20 mg of compound of formula (I) or pharmaceutically acceptable salt thereof calculated as the free base, the composition being administered 1 to 6 times per day.

The following Examples illustrate the invention.

EXAMPLES

EXAMPLE 1

2-[2-(2-Guanidino-4-thiazolylmethylthio)ethylamino]-3-nitropyrrole

A solution of 2-(2-guanidino-4-thiazolylmethylthio)-ethylamine dihydrochloride (4 g, 0.013 mole) in ethanol (25 ml) was basified with a solution of sodium (0.65 g, 0.028 mole) in ethanol (20 ml). The mixture was filtered and the filtrate added to 2-methylsulphinyl-3-nitropyrrole (1.5 g, 0.0086 mole). The mixture was refluxed for 5 days, then the solvent was removed in vacuo and the residue chromatographed on a silica-gel column. The product was eluted with ethyl acetate/propan-2-ol (8:2) and recrystallised from methanol/acetone (6:4). Yield: 0.65 g, 22%. M.P. 195.5°–200° C.

EXAMPLE 2

2-[2-(2-Guanidino-4-thiazolylmethylthio)ethylamino]-4-methyl-3-nitropyrrole

The title compound is prepared from 2-(2-Guanidino-4-thiazolylmethylthio)-ethylamine dihydrochloride and 2-methylsulphinyl-4-methyl-3-nitropyrrole by a process analogous to that described in Example 1.

EXAMPLE 3

2-[4-(2-Guanidino-4-thiazolyl)butylamino]-3-nitropyrrole

The title compound is prepared from 4-(2-guanidino-4-thiazolyl)butylamine dihydrochloride and 2-methylsulphinyl-3-nitropyrrole by a process analogous to that described in Example 1.

EXAMPLE 4

Preparation of pharmaceutical composition for oral administration

A pharmaceutical composition is prepared containing:

|   |   | % w/w |
|---|---|---|
| A | The product of Example 1 | 55 |
|   | Dibasic calcium phosphate dihydrate | 20 |
|   | Approved colouring agent | 0.5 |
|   | Polyvinylpyrrolidone | 4.0 |
| B | Microcrystalline cellulose | 8.0 |
|   | Maize starch | 8.0 |
|   | Sodium starch glycollate | 4.0 |
|   | Magnesium stearate | 0.5 | by mixing together the ingredients A (substituting lactose or microcrystalline cellulose for dibasic calcium phosphate dihydrate if desired), adding a concentrated solution of polyvinylpyrrolidone, and granulating, drying and screening the dried granules; adding the ingredients B to the dried granules and compressing the mixture into tablets, containing an amount of product corresponding to 100 mg, 150 mg or 200 mg of the free base.

EXAMPLE 5

Preparation of pharmaceutical composition for topical administration

A pharmaceutical composition is prepared containing:

|   |   | % w/w |
|---|---|---|
| A | The product of Example 1 | |
|   | Stearyl alcohol | 15.0 |
|   | Beeswax | 8.0 |
|   | Sorbitan monooleate | 1.25 |
|   | Polyoxyethylene sorbitan monooleate | 3.75 |
| B | The product of Example 1 | 1.0 |
|   | Sorbitol solution B.P. | 7.5 |
|   | Citric acid | 0.2 |
|   | Sodium citrate | 0.05 |
|   | Methylparaben | 0.18 |
|   | Propylparaben | 0.02 |
|   | Water to | 100 |

A mixture of the ingredients A is heated to 72° and added with stirring to a mixture of the ingredients B at 70°, and the stirring is continued until a cream is formed.

We claim:

1. A compound of formula

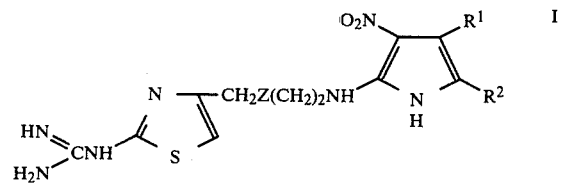

or pharmaceutically acceptable acid addition salt thereof, where Z is sulphur or methylene and $R^1$ is hydrogen; $C_{1-4}$ alkyl; optionally substituted phenyl or phenyl ($C_{1-4}$ alkyl), (the substituents being one or more $C_{1-4}$ alkyl or $C_{1-4}$ alkoxy groups or halogen atoms or a methylenedioxy group); or optionally substituted furanyl- or thienyl- or pyridyl-($C_{1-4}$ alkyl) (the substituents being one or more $C_{1-4}$ alkyl or $C_{1-4}$ alkoxy groups); and $R^2$ is hydrogen; $C_{1-4}$ alkyl or benzyl.

2. A compound according to claim 1 where $R^1$ is 3-methylphenyl; 3-methoxyphenyl; 3,4-dimethoxyphenyl or 3-chlorophenyl.

3. A compound according to claim 1 where $R^1$ is an optionally substituted 2-furanyl-, 2-thienyl-, 3-pyridyl- or 4-pyridyl ($C_{1-4}$ alkyl) group.

4. A compound according to claim 3 where $R^1$ is 3-pyridyl-, 6-methyl-3-pyridyl-, or 6-methoxy-3-pyridyl($C_{1-4}$ alkyl).

5. A compound according to claim 1 where $R^1$ is hydrogen.

6. A compound according to claim 1 where $R^2$ is hydrogen.

7. A compound according to claim 1 where Z is sulphur.

8. The compound according to claim 1 which is 2-[2-(2-guanidino-4-thiazolylmethylthio)ethylamino]-3-nitropyrrole.

9. The compound according to claim 1 which is 2-[2-(2-guanidino-4-thiazolylmethylthio)ethylamino]-4-methyl-3-nitropyrrole.

10. The compound according to claim 1 which is 2-[2-(2-guanidino-4-thiazolylmethylthio)butylamino]-3-nitropyrrole.

11. A pharmaceutical composition having histamine $H_2$-receptor blocking activity comprising in an amount effective to block said receptors a compound of claim 1 and a pharmaceutically acceptable carrier.

12. A method of blocking histamine $H_2$-receptors which comprises administering to an animal an effective amount to block said receptors of a compound of claim 1.

* * * * *

UNITED STATES PATENT AND TRADEMARK OFFICE
CERTIFICATE OF CORRECTION

PATENT NO. : 4,359,466

DATED : November 16, 1982

INVENTOR(S) : Michael L. Roantree and Rodney C. Young

It is certified that error appears in the above—identified patent and that said Letters Patent is hereby corrected as shown below:

On the title page of the patent, in the left-hand column, following item [22] insert:

[30]  Foreign Application Priority Data

October 24, 1979     United Kingdom 36810

Signed and Sealed this

Eleventh Day of January 1983

[SEAL]

Attest:

GERALD J. MOSSINGHOFF

Attesting Officer    Commissioner of Patents and Trademarks